US00PP37843P2

(12) United States Plant Patent
Schoenmakers

(10) Patent No.: US PP37,843 P2
(45) Date of Patent: Nov. 10, 2026

(54) ***FITTONIA* PLANT NAMED 'KEJAPA118'**

(50) Latin Name: *Fittonia verschaffeltii*
Varietal Denomination: KEJAPA118

(71) Applicant: Schoenmakers Tussenholding B.V., Haaren (NL)

(72) Inventor: Jan Cornelis Adrianus Maria Schoenmakers, Haaren (NL)

(73) Assignee: Schoenmakers Tussenholding B.V., Haaren (NL)

( * ) Notice: Subject to any disclaimer, the term of this patent is extended or adjusted under 35 U.S.C. 154(b) by 0 days.

(21) Appl. No.: 19/640,950

(22) Filed: Apr. 7, 2026

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan Mccormick Ewoldt
(74) *Attorney, Agent, or Firm* — Samuel R. McCoy, Jr.

(57) ABSTRACT

'KEJAPA118' is a new and distinctive *Fittonia* plant which is characterized by a compact and creeping growth habit, broad elliptic laminas, juvenile foliage with light-pink-on-light-yellow-green pinnately reticulate variegation, mature foliage with pink-on-dark-green pinnately reticulated variegation, mature foliage that transitions to bright-pink-on-greyed-purple pinnate variegation with prolonged exposure to ultraviolet light, and the stability of all characteristics from generation to generation.

2 Drawing Sheets

Latin name of the genus and species: The Latin name of the novel plant variety herein is *Fittonia albivenis* (Verschaffeltii Group), which is considered to be synonymous with *Fittonia verschaffeltii.*

Variety denomination: The inventive variety of *Fittonia* plant disclosed herein has been given the variety denomination 'KEJAPA118'.

BACKGROUND OF THE INVENTION

Parentage: The claimed plant, 'KEJAPA118', originated as a naturally occurring partial-plant mutation of *Fittonia albivenis* 'Pink Special' (not patented), which was discovered growing amongst a cultivated population at a commercial greenhouse in Haaren, The Netherlands, in May of 2021. The mutation was noted for its unique foliar coloration and variegation pattern, relative to its parent. The mutation was harvested from the parent plant and subsequently propagated by rooting stem cuttings. The resulting plants were then grown to a mature size in order to evaluate and confirm the uniformity and stability of the unique characteristics first observed. Upon confirmation, in May 2022, the inventor selected the claimed *Fittonia* plant 'KEJAPA118'.

Asexual Reproduction: Asexual reproduction of 'KEJAPA118' by way of rooting stem cuttings, was first performed in May of 2021 at a commercial greenhouse in Haaren, The Netherlands. Through eight subsequent generations, the plants so produced have shown that the unique features of the instant cultivar are stable and reproduced true to type.

SUMMARY OF THE INVENTION

The cultivar 'KEJAPA118' has not been observed under all possible environmental conditions, and the phenotype may vary somewhat with variations in the instant environment such as temperature, day length, and light intensity, without, however, any variance in genotype. The following characteristics have been repeatedly observed and represent the distinguishing characteristics of the new *Fittonia* cultivar 'KEJAPA118'. These traits, in combination, distinguish 'KEJAPA118' as a new and distinct cultivar.

1. *Fittonia* 'KEJAPA118' exhibits a compact, creeping growth habit with broad elliptic laminas; and
2. *Fittonia* 'KEJAPA118' exhibits a juvenile adaxial foliar surface with a light-pink-on-light-yellow-green pinnately reticulate variegation pattern; and
3. *Fittonia* 'KEJAPA118' exhibits a mature adaxial foliar surface with a pink-on-dark-green, pinnately reticulated variegation pattern; and
4. *Fittonia* 'KEJAPA118' exhibits a mature adaxial foliar surface that becomes progressively suffused with greyed-purple with prolonged exposure to ultraviolet light, creating a bright-pink-on-greyed-purple pinnate variegation pattern.

BRIEF DESCRIPTION OF THE FIGURES

The following photographs were taken using conventional techniques and although colors may appear different from actual colors due to light reflectance, it is as accurate as possible by conventional photographic techniques.

BOTANICAL DESCRIPTION OF THE PLANT

Figure 1:
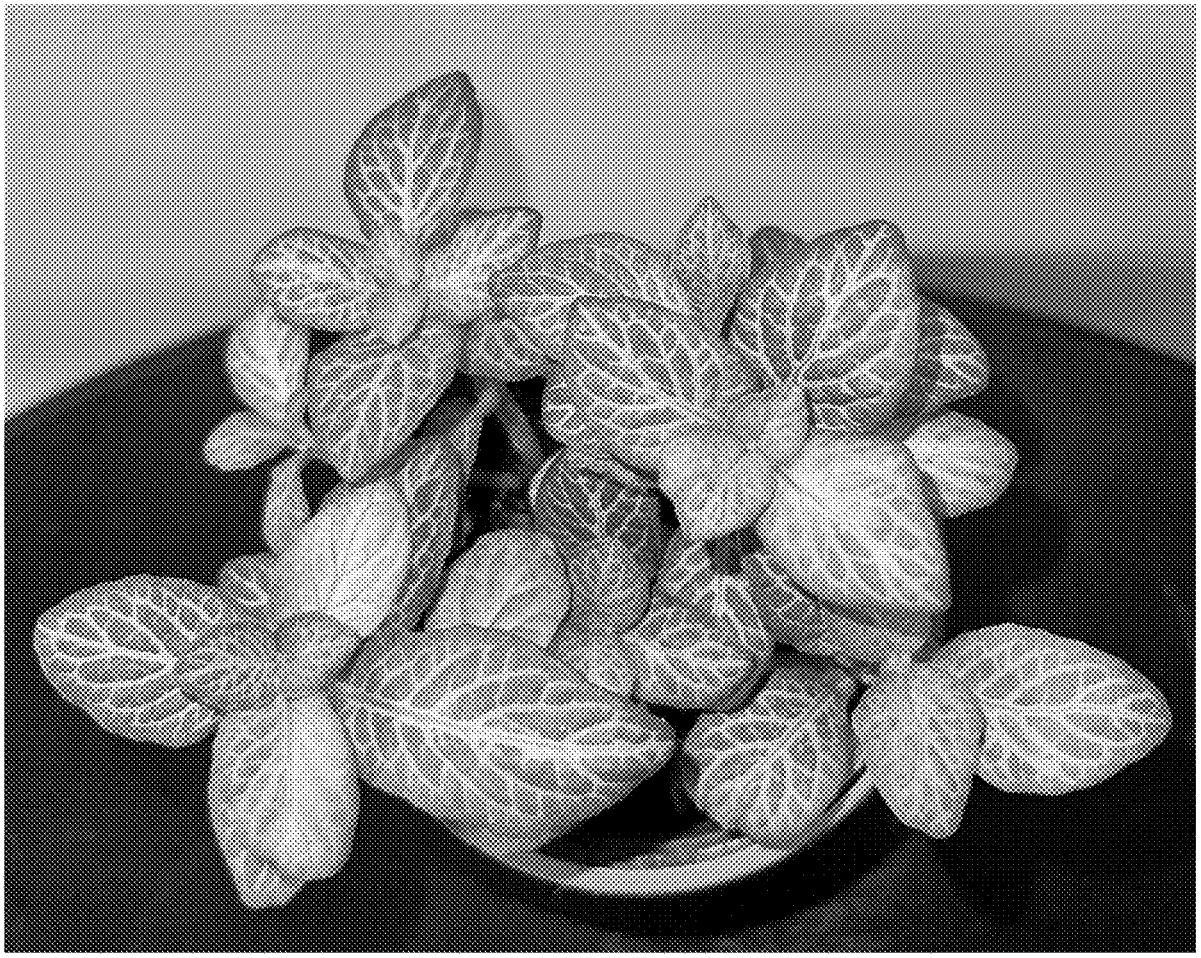
FIG. 1 shows, as nearly true as it is reasonably possible to make the same in color illustrations of this type, an exemplary plant of the new cultivar, 'KEJAPA118', approximately 23-week-old in a 350 mL nursery container. The plant shown was grown from a rooted cutting, potted into a nursery container, grown in a greenhouse in Stuarts Draft, Virginia under approximately 2,000 to 4,000 lumens of ultraviolet light.
Figure 2:
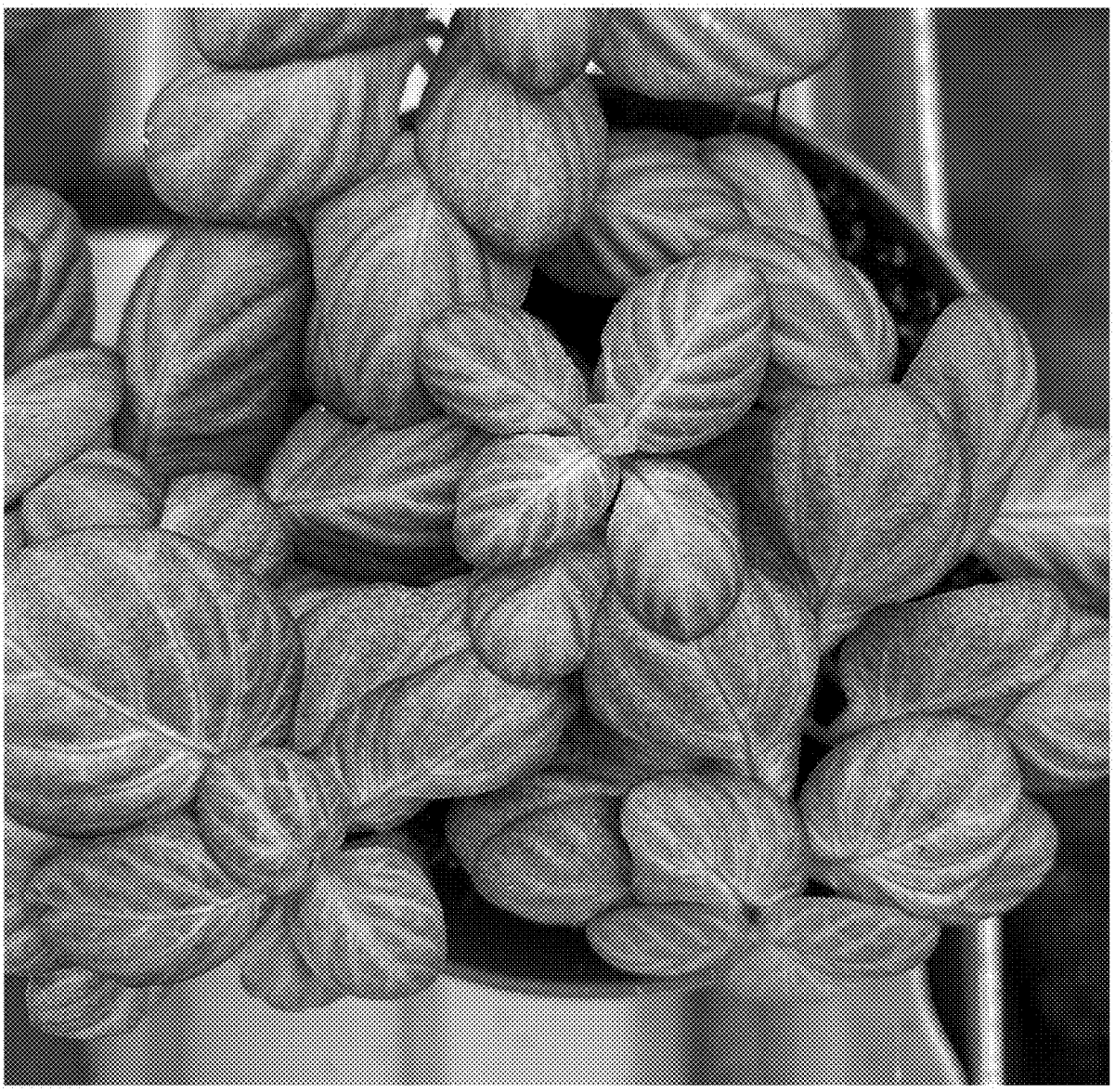
FIG. 2 shows, as nearly true as it is reasonably possible to make the same in color illustrations of this type, a 20-week-old greenhouse-grown 'KEJAPA118' in a 350 mL nursery container. The plant shown was grown using the same production protocols as the plant in FIG. 1, only they were grown under approximately 4,000 to 6,000 lumens of ultraviolet light.

The following observations and measurements were made in September of 2025. With the exception of the 20-week-old plants grown under higher light levels which were used to describe the mature adaxial foliar red foliar suffusion, the *Fittonia* 'KEJAPA118' plants described in this botanical description are approximately 23-week-old grown in a 350 mL nursery container. Plants were produced using conventional greenhouse production protocols for *Fittonia* species which consisted of overhead irrigation once a week, grown under shade with light levels ranging from approximately 2,000 to 4,000 lumens, with ambient temperatures ranging from 20 to 35 degrees Celsius and humidity levels ranging from 60 to 95 percent. No pest or disease measures were employed.

Those skilled in the art will appreciate that certain characteristics will vary with older or, conversely, with younger plants. 'KEJAPA118' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on *The Royal Horticultural Society Colour Chart*, The Royal Horticultural Society, London, Second Edition.

A botanical description of 'KEJAPA118' and comparisons with the parent plant and the most similar variety of common knowledge are provided below.

Plant description:

*Growth habit*.—Compact, creeping perennial.

*Height*.—7.8 cm.

*Width*.—17.1 cm.

*Propagation*.—Type — Asexual propagation is accomplished by way of rooting stem cuttings. Time to produce a rooted cutting — Approximately 4 weeks to produce a rooted cutting. Time to produce a rooted mature plant — Approximately 14 to 20 weeks grown in a 350 mL nursery container.

*Disease resistance*.—'KEJAPA118' exhibits susceptibility in common with the parent including bacterial leaf spot caused by *Xanthomonas campestris*, fungal blight caused by *Rhizoctonia solani*, as well as common arthropod pests such as aphids, moths, fungus gnats, and thrips.

*Environmental tolerances*.—Adapt to temperatures as high as 31 degrees Celsius. Thrives in partial shade with 60 to 70 percent humidity. Leaf scorch will occur in direct sunlight. 'KEJAPA118' requires irrigation once every 5 to 7 days and prefers growing under 50 $\mu mol/m^2/s$ shaded light.

Root system:

*General*.—Shallow, fibrous root system; stoloniferous.

*Texture*.—Smooth and glabrous.

*Color*.—Greyed-orange, nearest to RHS 165D.

Stem:

*General branching habit*.—Basally branching main stems; with decumbent lateral branches, or stolons, that root at the nodes when in contact with the soil.

*Main stem*.—Length — 4.8 cm. Diameter — 0.4 cm. Internode length — 1.9 cm. Texture — Coriaceous and pubescent, with white trichomes present, closest to RHS 155A; trichomes are approximately 0.7 mm in length. Luster — Glossy. Color of developing stems — Yellow-green, nearest to a combination of RHS 144B and 144C, and suffused with greyed-red, RHS 181C. Color of mature stems — Yellow-green, nearest to a combination of RHS 144B and 144C, and very lightly suffused with greyed-red, RHS 180A.

*Stolons*.—Length — 4.2 cm. Diameter — 0.3 cm. Internode length — 1.8 cm. Attitude — Decumbent. Cross-section — Terete. Texture — Coriaceous and pubescent, with white trichomes present, closest to RHS 155A; trichomes are approximately 0.1 cm in length. Color — Yellow-green, nearest to a combination of RHS 144B and 144C, and very lightly suffused with greyed-red, RHS 180A. Color at internodes — Yellow-green, nearest to a combination of RHS 144B and 144C.

Foliage:

*Arrangement*.—Opposite.

*Attachment*.—Petiolate.

*Division*.—Simple.

*Lamina*.—Shape — Broad elliptic. Length — 3.8 cm. Width — 2.9 cm. Apex — Acute; often curling downward. Base — Acute. Cross-section — Concave. Attitude — Varying from semi-erect to near-horizontal. Margin — Sparsely and shallowly crenate. Texture and luster of the adaxial surface — Glabrous and matte. Texture and luster of the abaxial surface — Glabrous and matte with salient veins. Color — Juvenile foliage, adaxial surface — Yellow-green, nearest a combination of RHS 144B and 146C, and transitioning to RHS 144A at and near the margins and apex. The entire network of veins, including the majority of the cross-venulate tertiary veins, is narrowly margined with red-purple, a combination of RHS 62A, 62D, and 63D which creates a light-pink-on-light-yellow-green pinnately reticulate variegation pattern. Juvenile foliage, abaxial surface — Yellow-green, nearest to RHS 148C. Mature foliage, adaxial surface — Yellow-green, nearest to a combination of RHS 144A, 147B, and 147C. The main vein, lateral veins, and a portion of the tertiary veins are margined with varying shades of light red-purple, nearest to a combination of RHS 62A, 62C, and 63C; the marginal portions of the lateral veins are nearest to RHS 62A. This margining of the venation creates a pink-on-dark-green, pinnately reticulated variegation pattern. With prolonged exposure to ultraviolet light, the entire lamina becomes moderately suffused with greyed-purple, RHS 186A, which creates the effect of a bright-pink-on-greyed-purple pinnate variegation pattern. Mature foliage, abaxial surface — Green, in between RHS 138B and 138C. Venation — Pattern — Pinnately reticulate. Color — Juvenile foliage, adaxial surface — At and very near the point of attachment to the petiole, the main vein is greyed-red, nearest to RHS 186B, while the remainder of the main vein and all other veins are red-purple, RHS 63C. Juvenile foliage, abaxial surface-Yellow-green, nearest to RHS 145C. Mature foliage, adaxial surface — At and very near the point of attachment to the petiole, the main vein is greyed-red, nearest to RHS 186B, while the remainder of the main vein and all other veins are red-purple, a combination of RHS 62A and 62D. Mature foliage, abaxial surface — Yellow-green, nearest to RHS 145C.

*Petiole*.—Length — 1.0 cm. Diameter — 0.1 cm. Strength — Strong. Texture — Smooth; glabrous. Luster — Glossy. Color, adaxial surface — Yellow-green, nearest to a combination of RHS 144B and 144C. Color, abaxial surface — Yellow-green, nearest to a combination of RHS 144B and 144C.

Inflorescence: No flowering has been observed to date.

COMPARISONS WITH THE PARENT PLANT

Plants of the new cultivar 'KEJAPA118' may be distinguished from the parent plant, of *Fittonia albivenis* 'Pink Special' (not patented), by the characteristics described in Table 1.

TABLE 1

Comparison between 'KEJAPA118' and 'Pink Special'

| Characteristic | 'KEJAPA118' | 'Pink Special' |
|---|---|---|
| Lamina shape. | Broad elliptic. | Oval to spatulate. |
| Foliage cross section. | Sparsely and shallowly crenate; no undulation. | Entire to repand; lightly undulated. |
| General expression of the variegation pattern, juvenile foliage. | Light-pink-on-light-yellow-green pinnately reticulate variegation pattern. | Bright-red-purple-on-yellow-green pinnately reticulate variegation pattern. |
| General expression of the variegation pattern, mature foliage. | Pink-on-yellow-green pinnately reticulate variegation pattern. | Bright-red-purple-on-dark-red-purple pinnately reticulate variegation pattern. |

TABLE 1-continued

Comparison between 'KEJAPA118' and 'Pink Special'

| Characteristic | 'KEJAPA118' | 'Pink Special' |
|---|---|---|
| | | variegation pattern. |

COMPARISONS WITH THE MOST SIMILAR COMMERCIAL VARIETY

Plants of the new cultivar 'KEJAPA118' may be distinguished from the most similar commercial comparator known to the inventor, *Fittonia albivenis* 'Bubble Red' (Community Plant Variety Rights application number 2009/0568), by the characteristics described in Table 2.

TABLE 2

Comparison Between 'KEJAPA118' and 'Bubble Red'

| Characteristic | 'KEJAPA118' | 'Bubble Red' |
|---|---|---|
| Lamina shape. | Broad elliptic. | Oval. |
| Foliar margins. | Sparsely and shallowly crenate. | Entire. |
| General expression of the variegation pattern, juvenile foliage. | Light-pink-on-light-yellow-green pinnately reticulate variegation pattern. | Red-purple-on-green pinnate variegation pattern. |
| General expression of the variegation pattern, mature foliage. | Pink-on-yellow-green pinnately reticulate variegation pattern. | Red-purple-on-dark-green pinnate variegation pattern. |

That which is claimed is:

1. A new and distinct variety of *Fittonia* plant named 'KEJAPA118', substantially as described and illustrated herein.

* * * * *